United States Patent [19]

Stephens et al.

[11] 4,438,070
[45] Mar. 20, 1984

[54] PACKED COLUMN THERMAL REACTOR FOR AN ANALYTICAL INSTRUMENT

[75] Inventors: Donald E. Stephens, Palo Alto; Thomas D. Sharples, Atherton, both of Calif.

[73] Assignee: Beckman Instruments, Inc., Fullerton, Calif.

[21] Appl. No.: 327,379

[22] Filed: Dec. 4, 1981

[51] Int. Cl.³ ............................................ G01N 31/08
[52] U.S. Cl. .................................... 422/70; 422/211; 422/240
[58] Field of Search ................. 422/211, 220, 70, 109, 422/199, 240; 436/52, 89, 90

[56] References Cited

U.S. PATENT DOCUMENTS

| | | | |
|---|---|---|---|
| 3,345,804 | 10/1967 | Mariani et al. | 55/67 |
| 3,471,261 | 10/1969 | Patterson | 23/230 |
| 3,806,321 | 4/1974 | Durrum et al. | 23/253 R |
| 3,846,074 | 11/1974 | Tulumello et al. | 422/70 |
| 3,865,555 | 2/1975 | Elebracht et al. | 23/288 R |
| 4,165,219 | 8/1979 | Huber | 23/230 R |

FOREIGN PATENT DOCUMENTS 3115873  1/1982  Fed. Rep. of Germany ........ 422/70
1249476 10/1971  United Kingdom .

OTHER PUBLICATIONS

LKB4400-The Benefits.
Durrum Amino Acid Analyzer D-500.
Model 3A29 Analyzer by Carlo Erba.
Biotronik Amino Acid Analyser LC 7000.
Chromaspek Instrument by Rank-Hilger.

Primary Examiner—Hiram H. Bernstein
Attorney, Agent, or Firm—R. J. Steinmeyer; F. L. Mehlhoff; T. R. Schulte

[57] ABSTRACT

An elongate straight column for use as a reactor in an analytical instrument. The column contains inert packed material which provides for the necessary flow path length for a fluid stream entering the reactor. Fittings are incorporated onto the ends of the column in such a manner that their width is no larger than the width of the column. The column configuration for a reactor allows more versatility in the type of temperature regulator mechanisms used to heat and cool the reactor.

1 Claim, 9 Drawing Figures

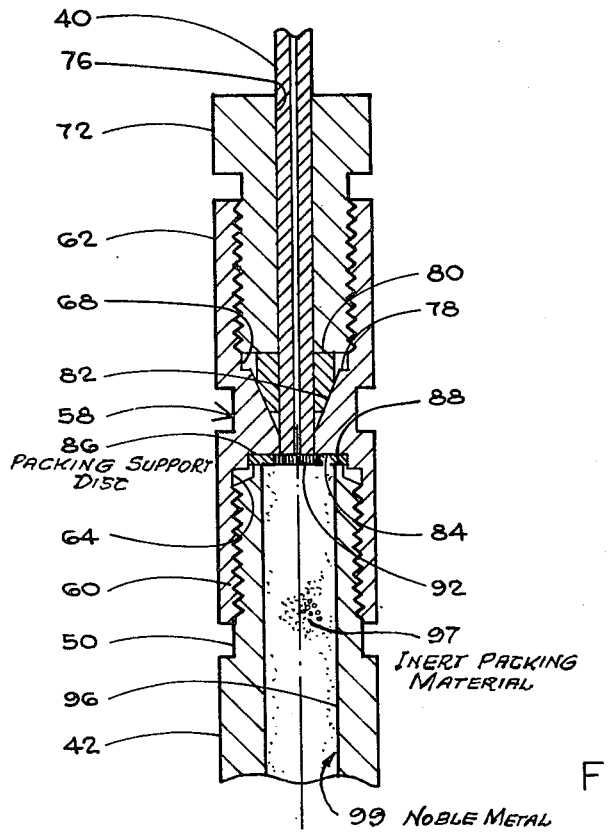
FIG. 4
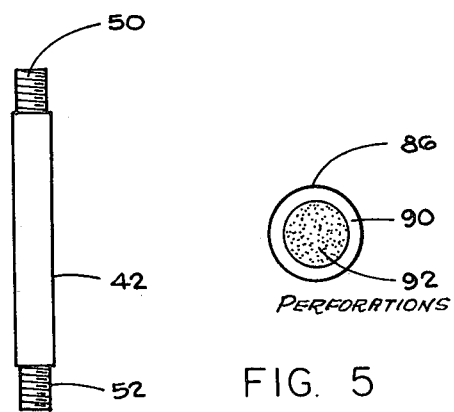
FIG. 3
FIG. 5

PACKED COLUMN THERMAL REACTOR FOR AN ANALYTICAL INSTRUMENT

BACKGROUND OF THE INVENTION

The present invention is directed to automated analyzers and, more specifically, is directed to a transport delay mechanism for use in a flowing stream reactor that may comprise part of an automated analyzing instrument. Color development in the detection system of an amino acid analyzer has been selected as a representative application.

In some amino acid analysers, a very small or micro chromatographic column is used as a specialized application of a liquid column chromatographic separation technique, utilizing ion exchange resin as the stationary phase and eluting buffers of varying pH and salt concentration as the moving phase. Amino acids contained in a sample are introduced at the top of the column and are separated from each other as they are eluted through the resin bed which comprises the column packing. For amino acid analysis, the method for detecting the amino acids in the effluent stream has been to combine the column effluent with a reagent that is metered into the stream at a flow rate proportional to that of the column eluent. When the reagent combines with the amino acids present in the stream, compounds are formed which, when subjected to further development process, can be detected by specific changes in optical properties such as absorption or fluorescence.

One of the classical detection methods in amino acid analyzer systems is that developed by Spackman and Moore, wherein the reagent used is ninhydrin dissolved in a suitable solvent/buffer solution. Under this process, the column effluent/reagent solution is heated in a reactor to a fixed temperature for a specified period of time. The compound developed as a result of this process will have specific colors, the intensities of which are proportional to the amounts of compounds contained in the flowing stream. The optical density of these compounds is measured at specific wavelengths.

Important to the calibration of the analyzer in terms of its specific sensitivity to detect amino acids is that the fluid/reagent mixture be maintained at a constant elevated temperature for a fixed period of time. It is critical to the stability of the instrument calibration that the two parameters of temperature and exposure time remain constant during the color development process. Classically, this has been accomplished by causing the effluent to pass through a TFE Teflon capillary coil which is normally suspended in a boiling water bath to act as the reactor in the amino acid analyzer system.

The separation techniques employed in early analyzers required several hours to complete a single analysis. In such systems, it became common practice to retain the flowing stream within the reactor for as long as fifteen minutes to complete the color development. Newer techniques have increased the performance of these analyzers to permit the same analyses to be completed in the order of twenty minutes. It has then becomd necessary to provide increased color development in a much shorter period of time. Reference is made to FIG. 1 showing empirical results of studies which relate the optical densities of compounds formed by mixtures of ninhydrin and amino acids as a function of development time and temperature.

It may be noted that maximum sensitivity and improved resolution can be obtained by operating the color development reactor at temperatures significantly above 100° C. However, operation at these elevated temperatures obviates the use of TFE Teflon capillaries immersed in boiling water as has been done in prior analyzers. It then becomes necessary to develop a transport delay system within a heated zone for the flowing liquids which will withstand both the elevated temperature and the corrosive nature of the flowing stream. The elevated temperatures plus the fact that the pH of the solutions alternate between bases and acids increases the corrosive attack by the liquids. Also, at these high temperatures, it is important that the reactor not be damaged by the heat; therefore, the system must provide rapid cooling of the reactor in the event there is some type of catastrophic loss of fluid flow caused by a loss of control in a system.

In most prior art the transport delay for the reactor has been a capillary coil that was usually wrapped in a cylindrical or spiral shape and located in some type of temperature control mechanism. The internal bore and length of this coil were of the proper dimensions to provide a suitable transport time within the heated zone at the flow rates prevailing in the analyzer. However, this type of configuration for the reactor does result in certain limitations with respect to the type of heating that can be used. In most instances, some type of heated bath surrounding the capillary coil has been used. A primary disadvantage with these types of heating systems for reactors is the fact that the cooling capability is not sufficient to provide the protection at higher temperatures against possible boiling of the flowing stream or against damage to the reactor materials themselves.

Because of the numerous disadvantages accruing to the use of a heated reactor in which liquid is used as the heat exchange medium, the design of a reactor using a solid state heat exchange medium has been pursued. In such a development, it soon becomes apparent that the formation of a capillary system into a shape which will permit it to be thermally bonded to a solid state heat exchanger is both difficult and costly. In addition, the cost of fabricating such capillaries from materials which will withstand the gross of nature of the fluids to which they will be subjected in the analyzers is prohibitive for all but the most exotic applications.

Attention is directed to ex,emplary prior systems such as shown in the U.S. Pat. No. 3,806,321 wherein FIG. 5 shows the reaction coil that is used to provide the color development. Another type of reactor is shown in U.S. Pat. No. 4,233,030 wherein the coils are longitudinally doubled back over each other. The U.S. Pat. No. 3,918,907 patent refers to the conventional type of means used to heat the reactor as a reaction coil in an electrically heated boiling bath. Similarly, in U.S. Pat. No. 3,926,800 the color reaction or development coil 23 is placed in a heated bath 24 to develop the color of the column effluent and reagent delivered to the coil.

Attention is directed to copending application entitled "Analytical Instrument Reactor Temperature Regulator", Ser. No. 327,378, filed on Dec. 4, 1981 in the name of Donald E. Stephens and assigned to the assignee of the present patent application. This referenced patent application discloses an alternate method of heating a color development reactor which is in the form of a column.

SUMMARY OF THE INVENTION

The present invention relates to the use of a straight elongated column as a transport delay for a heated reactor in an automated analyzer. The column is packed with an inert material having a small particle size (70 microns) of limited size distribution. The packing ensures a uniform fluid velocity across a section of the column, hence avoiding the problem of laminar flow and its degrading effects upon the resolution of the analyzer. The packed column provides the same requirements which the small bore capillary coils of the prior art supply relative to the transport delay of the flow path within the reactor and the necessary limitation of laminar flow of the flowing stream.

When operating a color development reactor at temperatures above 100° C., the choice of materials that are able to stand such high temperatures and the range of pH involved is essentially limited to the use of noble metals, certain precious metal alloys and possibly a few difficult to fabricate exotic alloys. Consequently, the use of a short, comparatively large bore column which can be internally plated with or possibly constructed from a noble metal will provide a highly desirable reactor for use at high temperature. Also, the configuration of the column packed with an inert material provides a device that can be fabricated at a cost considerably below that of drawn capillary tubes which would have to be made of suitable noble metal materials.

The use of a column configuration which provides both the necesary transport delay as well as the necessary linear front of the flowing stream allows much more flexibility in the type of heating system utilized for the reactor. Because of the use of the column configuration, numerous heating systems could be used such as the prior approach of boiling water, the reactor type heating arrangements as discussed in U.S. Pat. No. 4,294,799, and the apparatus discussed in the previously referenced copending patent application entitled "Analytical Instrument Reactor Temperature Regulator".

Pursuant to the development of this invention, it has been demonstrated that a transport delay for a flowing stream can be formed by utilizing a short, relatively large bore column packed with a suitable fine grain material having a particle size distribution of narrow range. This column can be made to have superlative performance to a capillary coil with regard to process stream resolution while providing appreciably longer transport delay time than a capillary coil. The form factor of the column lends itself well to being heated and cooled by solid state heat exchange medium, and its fabrication from materials that will withstand the high temperature and corrosive nature of the process is relatively easily managed.

BRIEF DESCRIPTION OF THE DRAWINGS

FIG. 3 is a side elevation view of the column reactor of the present invention;

FIG. 4 is a sectional view of the fitting on one end of the column;

FIG. 5 is a top view of the packing support for the column;

DETAILED DESCRIPTION OF THE INVENTION

For exemplary purposes, the application of the present invention will be discussed with respect to its use in an amino acid analyzer system. In such a system it is necessary to control the temperature of the thermal reactor to provide desirable color develop ment relating to the flowing stream.

Figure 2:
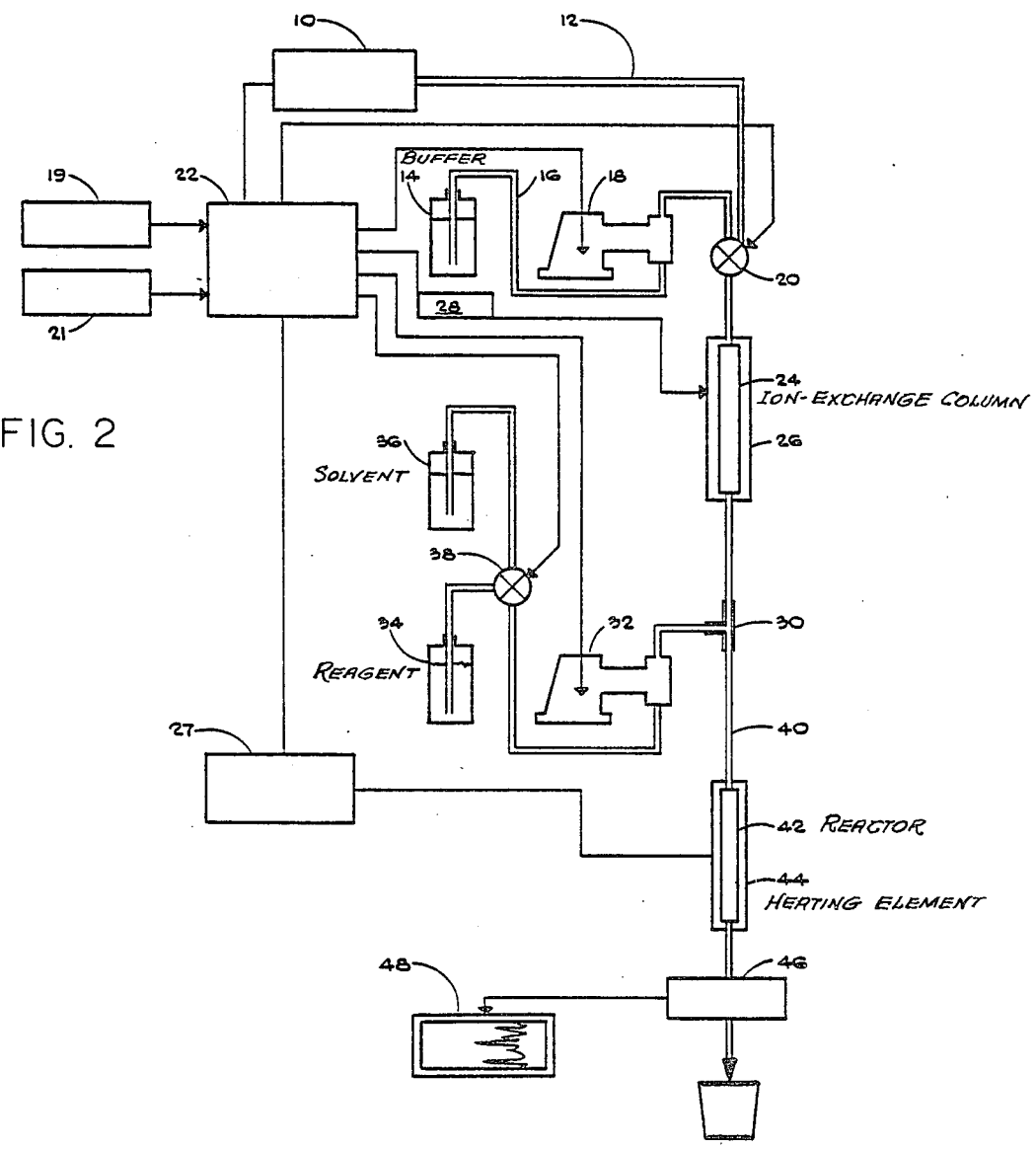
FIG. 2 is a schematic diagram of the overall amino acid analyzer system.

Attention is directed to FIG. 2, showing a schematic view of an overall amino acid analyzer system. A sample table 10 receives the various samples for introduction into the automated system which are sequenced through the conduit 12 to the sample injector valve 20. An eluting buffer 14 is transferred through the conduit 16 by the buffer pump 18 into the sample injector valve 20. The sample injector valve 20 is automatically operated by the analyzer controller 22 in order to sequence the sample in conjunction with the eluting buffer for introduction into the chromatographic column 24. As explained previously in the Background of the Invention, the liquid column chromatographic separation technique uses an ion exchange resin as a stationary phase with eluting buffers of varying pH and salt concentration as the moving phase. The resin base is packed into the column 24 for receipt of the eluting buffer in conjunction with the sample. The column 24 has a temperature regulator apparatus 26. A control system 28 is utilized to regulate the temperature in the column 24.

After the eluting stream exits the bottom of the column 24, it enters into a mixing tee 30 which is in fluid communication with a reagent pump 32 that is designed to pump the reagent 34 into the mixing tee 30. A solvent 36 is also used by operation of the valve 38 to pump solvent into the system which is done during shutdown procedures.

The reagent mixture with the eluting buffer 14 from the liquid chromatographic column 24 flows through the conduit 40 into a flow path in the reaction chamber or column 42. The compounds produced by the reagent mixing with the amino acids from the sample are subjected to further development in the reaction chamber where the mixed flowing stream is heated to a specific temperature for a specific time. The presence of these compounds is detected by noting specific changes in optical properties of the stream. The optical density at specific wavelengths will indicate the amounts of compounds present in the flowing stream. The photometer 46 is used to observe these colors and intensities while the recorder 48 provides a documented record.

Figure 1:
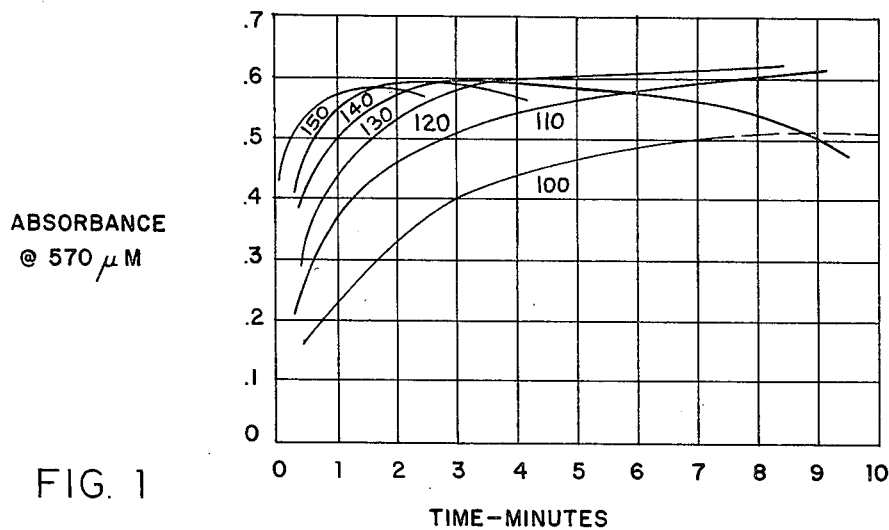
FIG. 1 is a graphic representation of color development of mixtures of amino acids and ninhydrins for variations in temperature and time.

Reference is made to FIG. 1 showing the results of some empirical studies made of the color development produced in ninhydrin/amino acid compounds under varying conditions of time and temperature. The graphical representation in FIG. 1 is a plot of optical density versus exposure time for a family of curves produced at different temperatures. This chart shows that maximum color development at 100° C. requires a dwell time approaching fifteen minutes within the reactor. However, equivalent development may be realized by heating the mixture to higher temperatures for shorter periods of time, for example, one minute at 135° C.

Attention is directed to FIG. 3 showing the column reactor 42 which is an elongated straight column preferably made of stainless steel or other corrosive resistant metals and having threaded ends 50 and 52 for interface with a fitting 58 shown in FIG. 4. The fitting 58 has a column receptacle end 60 and a flow line receptacle end 62. The interior of the column receptacle end 60 has an internal threaded cavity 64 for engagement with the threaded end 50 of the column 42. The flow line receptacle end 62 of the fitting 58 has an internal threaded cavity 68 for connection with a threaded connector screw 72. The center of the connector screw 72 has a bore 76 which is designed to receive the capillary line 40 which is in fluid communication with the mixing tee 30 as shown in FIG. 2.

Adjacent the bottom 78 of the internal threaded cavity 68 of the fitting 58 in FIG. 4 is a ferrule 80 which is designed to engage with the frustoconical recess 82 in the bottom 78 of the fitting flow line end 62. The ferrule 80 provides sealing of the capillary line 40 to the fitting 58. Movement of the connector screw 72 toward the bottom 78 of the cavity will compress the resilient ferrule and establish a tight seal.

Located adjacent the bottom 84 of the cavity 64 in the column end 60 of the fitting is a packing support disc 86 which is held in place by the edge 88 of the threaded end 50 of the column 42. While only one packing disc 86 is shown in FIG. 4, it should be understood that another packing support disc 86 is located at threaded end 52 of column 42. Attention is directed to FIG. 5 showing in more detail the column packing support 86 which has an annular solid portion 90 that is designed to provide a seal between the fitting 58 and the edge 88 of the threaded end 50 of the column. In the center portion 92 of the column packing support 86 in FIG. 5 are a plurality of perforations which are small enough to retain the column packing which is placed in the column, but are large enough to permit passage of the chromatographic effluent from the capillary path 40.

As shown in FIG. 4, the reactor or column 42 has an internal bore or passage 96 in which is placed a plurality of packing material such as diamond grit which has an approximate seventy micron size. It should be noted that diamonds have excellent thermal conductivity characteristics and do not insulate the heat being generated. This packing is placed in uniformity within the bore 96 to ensure a uniform velocity profile across the column section. The uniform arrangement of the packed particles will establish small passages which in total are smaller in cross section than the cross section of a capillary coil. This uniform arrangement in conjunction with the continual flow of the stream into the reactor will promote uniform travel or velocity of the stream throughout the cross section of the packed reactor bore, i.e., a uniform velocity profile.

It should be noted that the column 42 for use in a reactor in one application is, for example, 0.250 inches in diameter and approximately 2.4 inches long with a bore 96 of approximately 0.125 inches. Also, the interior surface of the column bore 96 is treated by electro-plating a noble metal such as platinum onto its surface.

Figure 6:
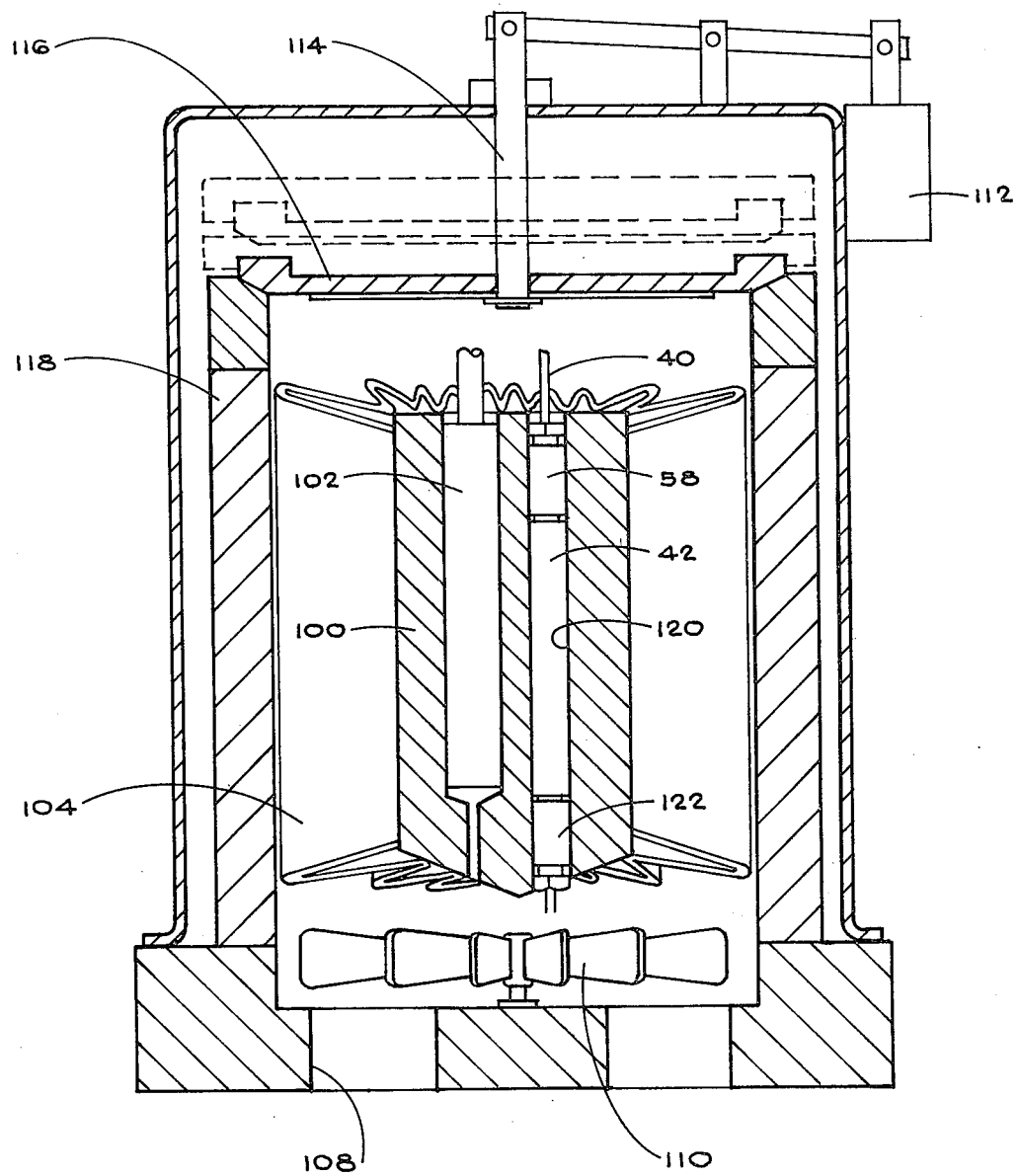
FIG. 6 is a sectional view of the column reactor configuration placed in a thermal regulator for the reactor.

With respect to the type of heating arrangements to which the present column is applicable, one approach for providing heat to a color development reactor is disclosed in the above referenced U.S. Pat. No. 4,294,799 which explains in detail the type of configuration shown in FIG. 6 of the present application for a packed column reactor. In the present invention, with respect to FIG. 6, the reactor 42 is placed within a heated core 100 which is preferably made of copper and is heated by a resistance element heater 102. A plurality of fins 104 is attached to the core element 100 to conduct heat into a flowing air stream which is drawn through the bottom opening 108 by the fan 110 during the cooling operation. By the control of the solenoid 112 and the damper mechanism 114, the lid 116 is lifted from the housing 118 to provide cooling by the circulating air when the reactor must be cooled. It should be noted that the column 42 is easily adapted for use with the core 100 by the construction of a cylindrical bore 120. This is especially true with respect to the fact that the fittings 58 and 122 are designed so that their diameter is no larger than the diameter of the column 42. This arrangement of a straight elongated column for placement in the heating mechanism greatly simplifies the heat transfer process as opposed to using a long capillary coil which must be either in the form of a spiral or in the form of some type of folded arrangement to provide the necessary transport delay in the reactor.

Figure 9:
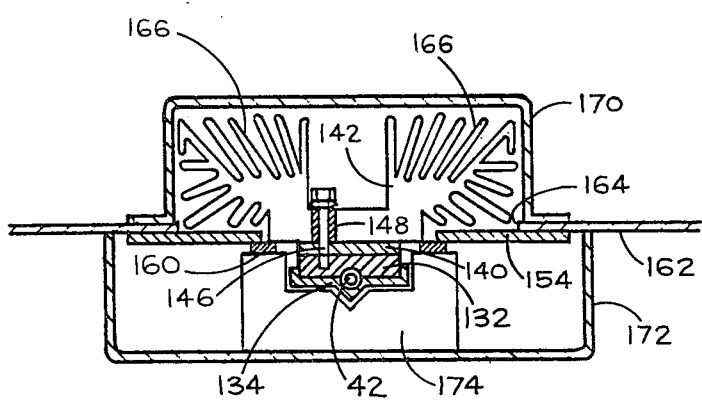
FIG. 9 is a sectional view taken along the lines 9—9 in FIG. 7.
Figure 8:
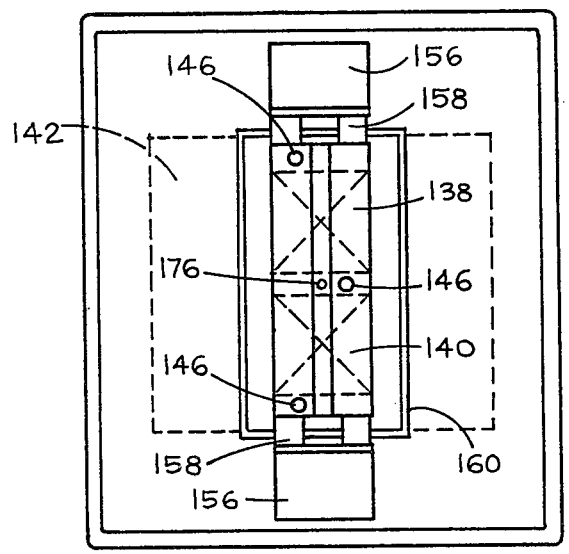
FIG. 8 is a front view of the temperature regulator of FIG. 7.
Figure 7:
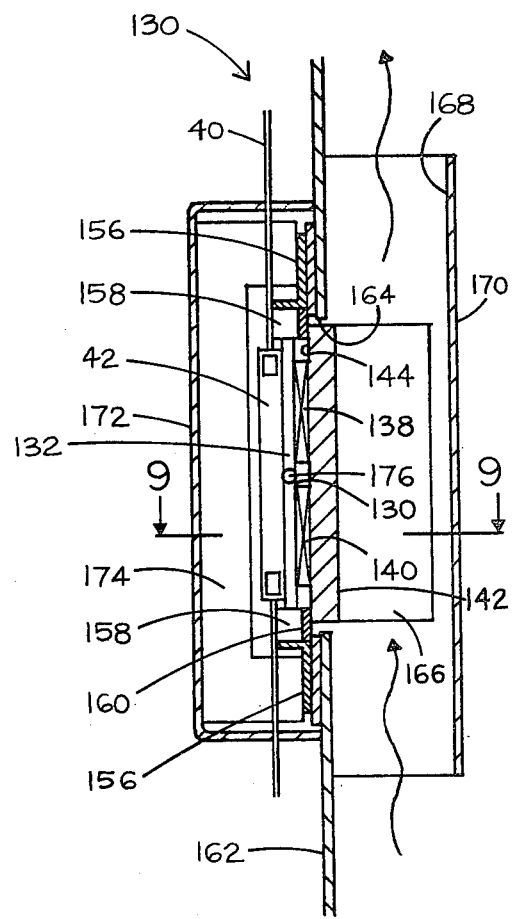
FIG. 7 is a sectional side view of another thermal regulator for the reactor.

Attention is directed to FIGS. 7–9 showing in more detail the arrangement of using thermoelectric elements for heating and cooling the reactor column. FIG. 7 shows more detail of the temperature regulator assembly 130 for the reactor 42. The reactor 42 is clamped to a thermal bar 132 by the use of the plate 134 shown in FIG. 9. The rear face 136 of the thermal bar 132 is ground flat and polished to provide an excellent thermal junction between the bar and two thermoelectric modules or devices 138 and 140 which are held in compression between the thermal bar 132 and a heat sink element 142. It should be noted that the face 144 of the heat sink is also polished smooth to provide a good thermal junction between the thermoelectric modules 138 and 140 and the heat sink. As shown more clearly in FIG. 8, three identical insulated mounting screws 146 are used to clamp the thermoelectric modules between the heat sink and the thermal bar 132. These mounting screws are stainless steel and are insulated from the heat sink by insulating sleeves 148 in FIG. 9. Compression washers 150 are also used on the mounting screws 146 to provide a calibrated force to the thermoelectric modules when the arrangement is assembled.

As shown in FIGS. 7 and 9, the reactor 42 and thermal bar 132 with the heat sink 142 are inserted through an aperture 152 in the mounting plate 154. Each end of the thermal bar 132 is attached to a mounting bracket 156 by stainless steel screws (not shown) inserted through insulators 158. This arrangement provides thermal isolation between the thermal bar 132 and the mounting plate 154. A flexible seal 160 is then inserted to cover the gap between the heat sink and the mounting plate. This construction provides that the thermal bar 132 is suspended from the mounting plate 154 while the heat sink is, in turn, suspended from the thermal bar. This type of support will remove all lateral stresses from the thermoelectric modules 138 and 140.

Once this overall system has been attached to the support wall 162, the heat sink 142 will protrude through a cutout opening 164 in the support wall 162. The plurality of heat exchange fins 166 in the heat sink member will be located in a plenum chamber 168 formed by the duct 170. Air leakage to the block is prevented by the seal 160. A cover member 172 having insulation material 174 is attached and surrounds the reactor and thermal bar as shown in FIGS. 7 and 9. A thermistor 176 is located in the central portion of the thermal bar 132 for sensing the temperature of the bar and to serve as a detector for the electrical control system which will control the operation of the thermoelectric modules 138 and 140. More specific detail relating to the control and operation of this temperature regulator is found in the previously referenced copending patent application entitled "Analytical Instrument Reactor Temperature Regulator" which is incorporated herein by reference.

Although various configurations have been shown with respect to the type of heating arrangements that can be utilized with a column reactor, it is envisioned that other types of heating arrangements could be utilized to conform with the unique versatility in using the present invention of a column for the reactor. Similarly, although one particular fitting arrangement has been shown, it is envisioned that other types of fittings could be designed to provide adequate sealing connection between the thin or small capillary line and the ends of the column reactor. Such other types of fittings could also be made wherein their overall diameter is no greater than that of the column itself.

What is claimed is:

1. A reactor for an automated analyzer, said reactor comprising:
   an elongate straight column including an interior surface defining a column bore;
   a noble metal electroplated onto said interior surface;
   externally threaded fittings on each end of said column for establishing fluid communication between said bore and said analyzer, said fittings being no wider than the width of said column;
   a pluarality of inert particles packed within said bore; and
   a packing support disc at each end of said column, said packing support disc having a plurality of small openings therein to allow fluid passage from one side of said disc to the other side of said disc, said openings small enough to retain said inert particles in said bore.

* * * * *